United States Patent [19]

Lewis et al.

[11] 4,140,602

[45] Feb. 20, 1979

[54] METHOD FOR OBTAINING CARBON DIOXIDE FROM THE ATMOSPHERE AND FOR PRODUCTION OF FUELS

[75] Inventors: John G. Lewis; Alfred J. Martin, both of Ann Arbor, Mich.

[73] Assignee: Texas Gas Transmission Corporation, Owensboro, Ky.

[21] Appl. No.: 671,945

[22] Filed: Mar. 30, 1976

Related U.S. Application Data

[63] Continuation-in-part of Ser. No. 609,833, Sep. 2, 1975, abandoned.

[51] Int. Cl.² ........................ B01J 1/10; C07C 5/02; C07C 29/16; C01F 5/24
[52] U.S. Cl. ........................ 204/157.1 H; 260/449.5; 260/683.9; 423/432
[58] Field of Search ............... 204/157.1 H, 158 H; 423/432; 260/449.5, 683.9

[56] References Cited

U.S. PATENT DOCUMENTS

| | | | |
|---|---|---|---|
| 1,862,176 | 6/1932 | Church et al. | 423/432 |
| 2,979,380 | 4/1961 | Miller | 423/432 |
| 3,558,724 | 1/1971 | Salotti | 260/676 R |
| 3,819,813 | 6/1974 | Jones et al. | 423/421 |
| 3,897,471 | 7/1975 | Herbert et al. | 260/449.5 |
| 3,940,324 | 2/1976 | Abramson et al. | 204/157.1 H |

Primary Examiner—Howard S. Williams
Attorney, Agent, or Firm—Laurence R. Brown

[57] ABSTRACT

The invention disclosed provides a new improved chemical method for combustible fuel production by converting carbon dioxide in the atmosphere to a carbonate following which the recovered carbonate is combined with hydrogen gas to produce combustible fuels e.g. methane and methanol. The present method provides means for fuel generation and may advantageously use heat and radiation energy derived from nuclear reactors.

This application implies certain environmental advantages, in that burning of fuels containing carbon derived only from atmospheric $CO_2$ would not add to the $CO_2$ content of the atmosphere. Recycling of lime as CaO or $Ca(OH)_2$ would eliminate the problem of disposing of those materials as encountered by others teaching use of carbonates but not using such a closed cycle.

17 Claims, 2 Drawing Figures

METHOD FOR OBTAINING CARBON DIOXIDE FROM THE ATMOSPHERE AND FOR PRODUCTION OF FUELS

This application is a continuation-in-part of Ser. No. 609,833 filed Sept. 2, 1975, now abandoned in favor of this application.

BACKGROUND

This invention relates to new improved methods of combustible fuel production. More particularly, the present invention provides an efficient means for the production of such fuels by a chemical process recovering carbon dioxide from the atmosphere following which it is combined with hydrogen to form the fuel.

A number of proposals have been made for using carbon dioxide to produce combustible fuels. Typically, these proposals have been commercially unattractive when the carbon dioxide is expendable such as when carbon monoxide becomes part of the combustible fuel because a source of carbon dioxide is necessary and some processes require inefficient amounts of energy. A further source of inefficiency is encountered when carbonates are used as a source of carbon dioxide, since chemical impurities are present and carbonates must ordinarily be ground and even then fail to be fine enough to produce large surface areas for reacting with other chemicals in an efficient process.

OBJECTS AND BRIEF DESCRIPTION

It is one object of this invention to derive carbon dioxide from the atmosphere or other source of $CO_2$ containing gas.

It is another object of this invention to produce combustible fuels from non-fossil sources.

It is a more specific object of this invention to provide a chemical cycle in which carbon dioxide may be converted from the atmospheric gas and recovered in a finely divided carbonate which can be reacted with hydrogen to provide combustible fuels.

It has now been found, that by practice of the present invention, there results a new improved method for combustible fuel production by extracting carbon dioxide from the atmosphere and forming a finely divided carbonate. The recovered carbonate is processed with hydrogen to form combustible fuels such as methane and methanol. Thus, commercially attractive methods are made available to the art for recovering carbon dioxide from the atmosphere and processing such to derive combustible fuels.

THE DRAWING

Practice of the present invention will become more apparent from the following detailed description taken in connection with the accompanying drawing wherein like numerals refer to similar elements.

FIG. 1 is a block diagram of the overall processing system of the present invention, and FIG. 2 is a block diagram of that part of the process for converting carbonates to combustible fuels.

DETAILED DESCRIPTION

Generally, the present method of deriving carbon dioxide from air is based on the following chemical reaction sequence:

$$2NaOH + CO_2 \xrightarrow{(atmosphere)} Na_2CO_3 + H_2O \quad \text{(I)}$$

$$Na_2CO_3 + Ca(OH)_2 \rightarrow 2NaOH + CaCO_3 \quad \text{(II)}$$

$$CaCO_3 \rightarrow CaO + CO_2 \quad \text{(III)}$$

$$CaO + H_2O \rightarrow Ca(OH)_2 \quad \text{(IV)}$$

$$4H_2 + CO_2 \rightarrow CH_4 + 2H_2O \quad \text{(V)}$$

$$CaCO_3 + 3H_2 \xrightarrow{\text{with catalyst}} CH_3OH + Ca(OH)_2 \quad \text{(VI)}$$

$$CaCO_3 + 4H_2 \xrightarrow{\text{with catalyst}} CH_4 + Ca(OH)_2 + H_2O \quad \text{(VII)}$$

Figure 1:
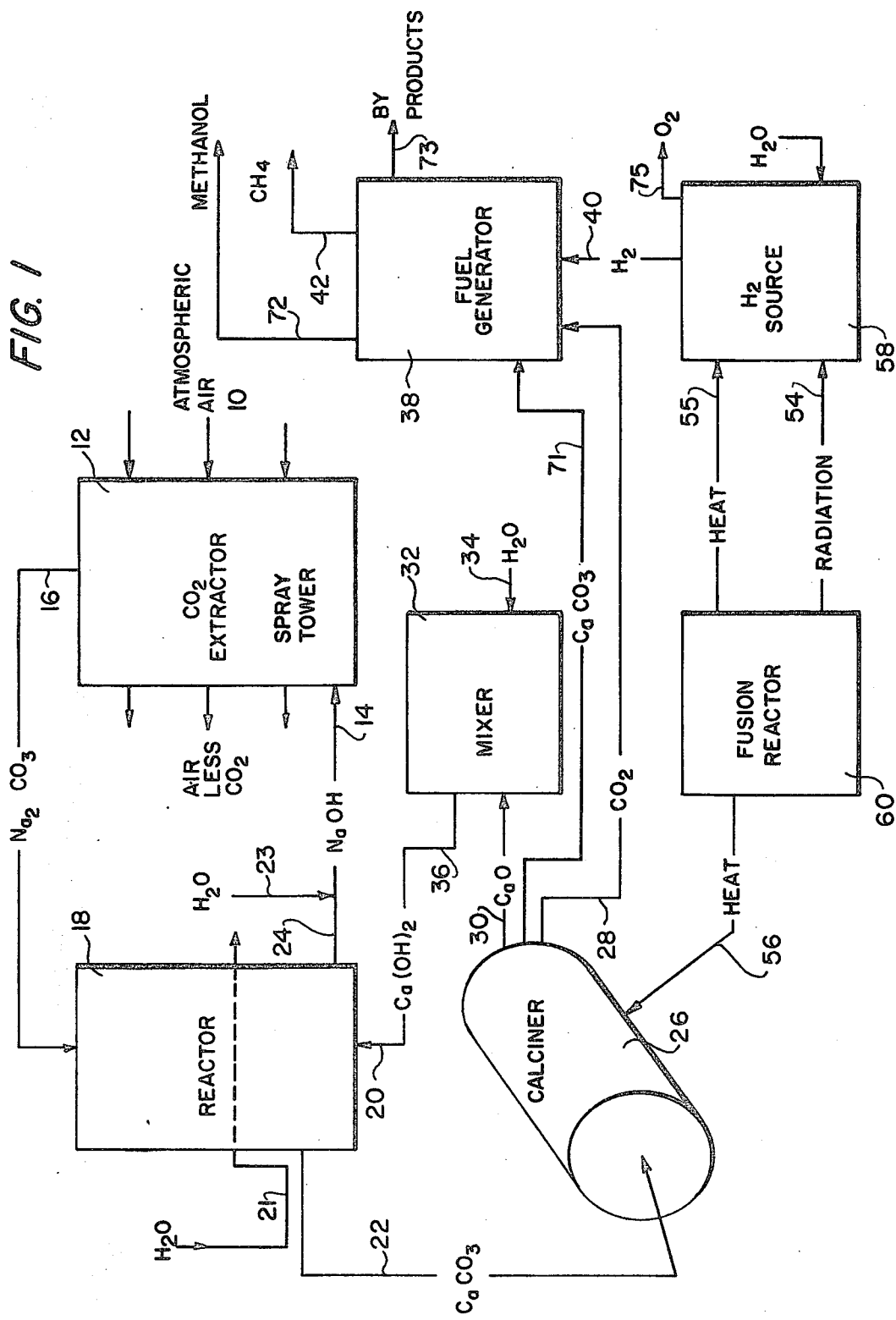

For use in the above reactions, and referring to FIG. 1, carbon dioxide is recovered in reaction (I) from the atmosphere by means of sodium hydroxide solution. For example, atmospheric air 10 carried by wind of 4 miles per hour or greater velocity may be passed into an open air spray field of sodium hydroxide solution having a concentration of about 0.1% by weight to about 0.5% by weight as exemplified by extraction unit 12. This unit comprises a spray tower construction wherein the water of the aqueous solution is sprayed into the atmosphere over a defined field to absorb carbon dioxide therefrom as heat is being rejected to the atmosphere by partial evaporation of the water during contact of the solution with the atmosphere. This provides a cooling feature aiding the reaction. Make up water is added at 23, and is preferably wash water used to remove any NaOH solution present in the $CaCO_3$ of stream 22, as indicated at 21.

The foregoing process when dependent upon the wind has the advantage that electric energy is not dissipated in pumping air through the solution. For use in the open atmosphere to obtain large production quantities consider the following example. A 67,000 brake horsepower pump raises the water pressure to 200 feet (86 pounds per square inch) and pumps water through a 16 foot diameter pipe to a spray area one mile long perpendicular to the prevailing wind and 1600 feet wide. Two hundred towers on 200 feet centers are placed in the spray area each about 150 feet high with 40 nozzles delivering 100 gallons per minute at the top aimed upward and outward to let a fine spray solution fall to the earth while absorbing $CO_2$. A polyethylene cover in the spray area can convey the solution by gravity to a collecting point. Each tower serves to convey 4000 gallons per minute to its sprays.

With the air blowing at 4.5 miles per hour and two-thirds of the $CO_2$ being absorbed the yield is about 13000 lb. moles $CO_2$ per hour.

As diagrammatically shown, the sodium hydroxide solution enters extraction unit 12 by line or nozzle arrangement 14 from a source 24. The solution may be generated in reactor 18 from calcium hydroxide introduced at line 20 and reacted with the sodium carbonate introduced at line 16 derived from atmospheric air in extraction unit 12. Output materials generated are sodium hydroxide and calcium carbonate (II). Sodium hydroxide is separated out and passes line 24 for recycle to the extraction unit 12.

The calcium carbonate from reactor 18 is separated by known processes and passes line 22 to calciner 26, which in one preferred embodiment would be a fluidized bed calciner, wherein it is roasted for release of carbon dioxide and production of calcium oxide (III). Carbon dioxide is recovered and passes line 28 to reactor 38 where it reacts with hydrogen from line 40 for generation of methane (V) which passes to recovery line 42.

Also the fuel generator can derive methanol (VI) at line 72 from the finely divided pure $CaCO_3$ which would in this process step be derived chemically. The $CaCO_3$ may bypass the calciner or may be calcined to convert it to CaO and $CO_2$. Prior art methods are not efficient because the $CaCO_3$ is either relatively large, even after grinding, or impure and requires handling of more extensive amounts of by-product materials. Although it is known to make methane and other hydrocarbons from reaction of hydrogen with a carbonate (U.S. Pat. No. 3,558,724 — C. A. Salotti, Jan. 26, 1974) such have had significant problems without a source of pure finely divided $CaCO_3$. It is noted the by-product is the desired $Ca(OH)_2$ which can be introduced into reactor 18. The $Ca(OH)_2$ can contain catalytic material which becomes available with the $CaCO_3$ to promote the reaction of the carbonate with the hydrogen.

Calcium oxide from line 30 passes to mixer 32 where it is reacted with water from line 34. Calcium hydroxide (IV) from mixer 32 is recycled to reactor 18 thereby completing the reaction sequence.

Thus, the only input ingredients except for secondary losses used to produce the $CO_2$ are air and water, which are in plentiful supply at reasonable cost.

One useful source of hydrogen 58 which may be used in the present process is that derived from radiolysis such as where carbon dioxide is dissociated to carbon monoxide and oxygen. The carbon monoxide may then be reacted with water to form carbon dioxide and hydrogen. This process obtained by radiation from a fusion reaction 60 is disclosed for example in copending application Ser. No. 416,998 filed by Henry J. Gomberg, Nov. 13, 1973, now abandoned.

In the radiolysis reaction, the carbon dioxide can be recycled. Thus, the only feed material, namely water, is consumed through conversion to oxygen output 75 and hydrogen. It will be appreciated that both the radiation 54 and the heat 55 needed for the thermochemical reactions producing $H_2$ at 58 can be derived from a fusion reaction 60, which is preferred, as well as other forms of energy where radiation in the form of neutrons and gamma rays may be used. It is noted that some of the radiation and heat energy may be by-products from other uses of fusion reactors, since for example it is desirable in the presently disclosed system to keep the equipment for the heat and radiation exchange simple without exotic high heat techniques and excessive radiation shields. The current state of the art has much literature showing how to derive temperature ranges, and radiation techniques useful in the chemical cycles disclosed herein. For example, reference is made to *Advances in Nuclear Science & Technology*, Vol. 1, pp. 309-313, where a similar process has been reported in connection with fission energy sources.

In the illustrated method, radiolytic conversion may be effected by ignition and burn of fusion fuel such as deuterium-tritium (D-T) in pellet form. Although a number of different approaches are available, one that utilizes a source of energy from a laser and particular pellet configuration to achieve laser-fusion in a reaction chamber is especially useful. Patents which illustrate generally the apparatus which can be used in this type of system include U.S. Pat. Nos. 3,378,446; 3,489,645; and 3,762,992.

Thus, radiation 54 and heat energy 55 used in the hydrogen generator 58 may be derived from a laser-fusion reactor 60, for example, in a thermo-radiolytic reaction and the excess heat 56 generated may be applied to other processing locations and in particular to calciner 26.

It appears to be reasonably well-known to calcine fine $CaCO_3$ at roughly 1600° F. However, 1600° F. might be hotter than we would prefer to operate heat exchange surfaces. It could be preferable to burn some hydrogen in direct contact with the $CaCO_3$ in order to achieve heat input at elevated temperature such as 1600° F. Rough estimates indicate that approximately 35% of the hydrogen produced would be burned with co-product oxygen in order to remove enough $CO_2$ from $CaCO_3$ to form methane with the remaining 65% of the hydrogen. Alternatively if $CaCO_3$ were not so calcined but were instead reacted directly with hydrogen to form methane and calcium hydroxide, about 20-24% of the heating value of the hydrogen would be consumed in the process. It would be desirable to effect this reaction

$$CaCO_3 + 4H_2 \rightarrow CH_4 + Ca(OH)_2 + H_2O \qquad (VII)$$

at no higher temperature than roughly 950°-1000° F. Holding the temperature to that limit would tend to allow $Ca(OH)_2$ to form, conserving heat energy thereby. Limiting the temperature to 950°-1000° F. would also be desirable in limiting decomposition of methane, thereby improving the yield. Because of the fine particle size of the precipitated $CaCO_3$ and the catalyst carried in it the reaction accelerates sufficiently to proceed at lower temperatures.

Figure 2:
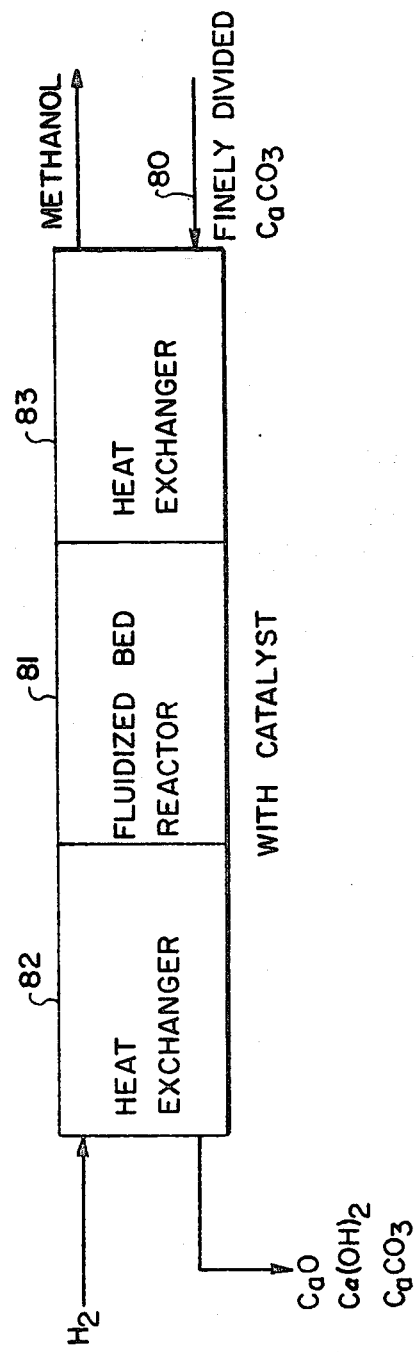

In FIG. 2 the process of providing methanol in accordance with this invention is shown. It is pertinent to make combustible fuels that $CaCO_3$ be supplied in industrial quantities in finely divided pure form which prior to this invention has not been deemed feasible. Thus input source 80 is critical to success of this phase of the invention.

It is noted that the previously mentioned U.S. Pat. No. 3,558,724 for example provides a teaching of the chemical reaction of hydrogen with $CaCO_3$ to produce hydrocarbons by static contact rather than taking place in the fluidized bed reactor 81. Also it may be noted that the flow directions of the raw materials $H_2$ and $CaCO_3$ are such that the inherent heat activity in the process are used together with external heat as necessary in the two heat exchangers 82, 83. The pressures are kept in the order of 50 atmospheres and the temperatures 500° to 600° F. The catalysts may include one or more of CuO, ZnO, $Cr_2O_3$ or $Al_2O_3$.

The primary advantage and efficiency of this phase is that a one step conversion between $CaCO_3$ and $H_2$ produces savings in equipment and input heat energy.

The basic equipment used in processing methanol from multiple stage converters is well known in the art as is fluidized bed reactor equipment.

Similar equipment is contemplated for the direct action

$$CaCO_3 + 4H_2 \rightarrow CH_4 + Ca(OH)_2 + H_2O \qquad (VII).$$

Although the present method has been illustrated generally by diagram, it will be apparent to those of the art that many variations may be made therein without departing from the essence of the features disclosed herein.

The reaction $CO_2 + 4H_2 \rightarrow CH_4 + 2H_2O$ is expected to proceed for example at 600°-650° F. over a reduced nickel catalyst. cf. W. W. Akers (last page). However, it is expected that reaction VII might be conducted at as high a temperature as 950°-1000° F. over for example a reduced nickel catalyst.

What is claimed is:

1. A method for producing combustible fuels from flow of a gaseous non-fossil mixture containing carbon dioxide, which comprises, extracting carbon dioxide from said gaseous flow by means of a solution forming a finely divided carbonate without mineral impurities, and converting the carbonate to a combustible hydrocarbon fuel.

2. The method of claim 1, wherein the gaseous flow is atmospheric air and the solution is sodium hydroxide sprayed through the air in a spray field.

3. The method of claim 2, wherein the carbonate formed is an alkali carbonate, including the additional step of reacting the alkali carbonate with calcium hydroxide to form calcium carbonate.

4. The method of claim 3, including additionally the step wherein calcium oxide is generated by heat decomposition of calcium carbonate and is reacted with water to form the solution.

5. The method of claim 3, wherein the calcium carbonate is obtained by reaction of the alkali carbonate with $Ca(OH)_2$.

6. The method of claim 5, wherein the calcium carbonate is obtained in finely divided form, and the finely divided calcium carbonate is reacted in a single step with $H_2$ to form methanol.

7. The method of producing methanol by reacting finely divided $CaCO_3$ without mineral impurities obtained in a chemical process from atmospheric gas flow through a spray field with $H_2$ in the presence of a catalyst to form methanol.

8. The method of extracting $CO_2$ from a gas mixture flow stream such as air of the atmosphere carried by wind which comprises passing the gas flow through a chemical solution reacting with $CO_2$ presented in an open spray field through which said atmospheric wind flows, and processing the resultant product formed by the chemical solution reaction with $CO_2$ with a chemical to form a carbonate which readily releases $CO_2$.

9. The method of claim 8 wherein said chemical is $Ca(OH)_2$.

10. The method of claim 9, wherein said carbonate is $CaCO_3$ a part being processed by burning with $H_2$ to obtain $CO_2$ and a part reacted with the $H_2$ to form methane.

11. The method of claim 8, wherein the chemical solution is NaOH.

12. The method of producing gaseous fuel from a gas such as air containing $CO_2$ and water comprising the steps of,
    separating $CO_2$ from the gas by reaction with an aqueous solution,
    reforming said aqueous solution for recycling by a reaction releasing a carbonate therefrom readily releasing $CO_2$,
    releasing said $CO_2$ from the carbonate,
    separating $H_2O$ into $H_2$ and $O_2$, and combining the $H_2O$ therefrom with said $CO_2$ to form a combustible fuel.

13. The method defined in claim 12, wherein the $H_2O$ is separated at least in part by radiation energy.

14. The method defined in claim 13, wherein radiation energy and heat required in the process are derived at least in part from a fusion reactor.

15. The method defined in claim 17, wherein said $CO_2$ is reacted with said solution to form a carbonate.

16. The method defined in claim 12 wherein the water of the aqueous solution is used as cooling water, heat being rejected to the atmosphere by partial evaporation of the water during contact of the solution with the atmosphere.

17. The method of producing combustible hydrocarbon fuel from air and water comprising the steps of,
    separating $CO_2$ from air by chemical reaction with an aqueous solution in a spray field through which the air is carried by wind to form a compound,
    removing $CO_2$ from said compound as a carbonate in finely divided form thereby reforming said aqueous solution for recycling,
    and combining $H_2$ with the carbonate in finely divided form to yield a combustible fuel consisting of methane, methanol and mixtures thereof.

* * * * *